(12) United States Patent
Guichard et al.

(10) Patent No.: US 7,972,060 B2
(45) Date of Patent: Jul. 5, 2011

(54) DENTAL RADIOLOGY IMAGE SENSOR WITH SOFT OVERMOLDING

(75) Inventors: Jérôme Guichard, Vatilieu (FR); Florian Julien, Voiron (FR)

(73) Assignee: E2V Semiconductors (FR)

( * ) Notice: Subject to any disclaimer, the term of this patent is extended or adjusted under 35 U.S.C. 154(b) by 91 days.

(21) Appl. No.: 12/594,875

(22) PCT Filed: Apr. 15, 2008

(86) PCT No.: PCT/EP2008/054529
§ 371 (c)(1),
(2), (4) Date: Oct. 30, 2009

(87) PCT Pub. No.: WO2008/135348
PCT Pub. Date: Nov. 13, 2008

(65) Prior Publication Data
US 2010/0116987 A1    May 13, 2010

(30) Foreign Application Priority Data
Apr. 20, 2007  (FR) ..................................... 07 02891

(51) Int. Cl.
*A61B 6/14* (2006.01)
*G01T 1/24* (2006.01)

(52) U.S. Cl. .................... 378/191; 378/98.8; 250/370.09

(58) Field of Classification Search ................ 378/98.8, 378/168, 169, 191; 250/370.09
See application file for complete search history.

(56) References Cited

U.S. PATENT DOCUMENTS

| 5,434,418 | A | * | 7/1995 | Schick | 250/370.11 |
| 5,691,539 | A | * | 11/1997 | Pfeiffer | 250/370.09 |
| 6,030,119 | A | | 2/2000 | Tachibana et al. | |
| 6,042,267 | A | * | 3/2000 | Muraki et al. | 378/169 |
| 6,309,101 | B1 | * | 10/2001 | Bacchetta et al. | 378/169 |
| 6,312,156 | B1 | * | 11/2001 | Bacchetta et al. | 378/169 |
| 6,320,934 | B1 | * | 11/2001 | Carroll et al. | 378/98.8 |
| 6,428,205 | B1 | * | 8/2002 | Bacchetta et al. | 378/169 |
| 6,579,007 | B1 | * | 6/2003 | Bacchetta et al. | 378/169 |
| 6,612,740 | B1 | * | 9/2003 | Resch et al. | 378/169 |
| 6,652,141 | B1 | * | 11/2003 | Cianciosi | 378/191 |
| 7,281,847 | B2 | * | 10/2007 | Kokkaliaris et al. | 378/189 |
| 7,309,158 | B2 | * | 12/2007 | Halevi | 378/191 |
| 7,563,026 | B2 | * | 7/2009 | Mandelkern et al. | 378/191 |
| 2006/0067462 | A1 | | 3/2006 | Hack | |
| 2007/0025523 | A1 | | 2/2007 | Halevi | |

FOREIGN PATENT DOCUMENTS

| EP | 1 661 518 | 5/2006 |
| EP | 1 699 232 | 9/2006 |
| WO | WO 00/29872 | 5/2000 |

* cited by examiner

*Primary Examiner* — Allen C. Ho
(74) *Attorney, Agent, or Firm* — Lowe Hauptman Ham & Berner, LLP

(57) ABSTRACT

The invention relates to an intra-oral dental radiology sensor. The sensor comprises an electronic image acquisition module and a molded casing made of a hard plastic which is locally provided with overmoldings made of a softer plastic having the consistency of smooth rubber, covering the hard plastic in areas located on the outside of the casing and corresponding to projecting angular portions of the hard plastic, and also in areas located inside the casing at places where the electronic module may bear. The soft plastic is preferably a copolymer of the SEBS (styrene/ethylene-butylene/styrene) type whereas the hard plastic is preferably a polyamide. The patient's comfort is improved and the module is better protected against shocks without increasing its size.

20 Claims, 2 Drawing Sheets

DENTAL RADIOLOGY IMAGE SENSOR WITH SOFT OVERMOLDING

CROSS-REFERENCE TO RELATED APPLICATIONS

The present Application is based on International Application No. PCT/EP2008/054529, filed on Apr. 15, 2008, which in turn corresponds to French Application No. 0702891, filed on Apr. 20, 2007, and priority is hereby claimed under 35 USC §119 based on these applications. Each of these applications are hereby incorporated by reference in their entirety into the present application.

FIELD OF THE INVENTION

The invention relates to an intra-oral dental radiology sensor.

BACKGROUND OF THE INVENTION

Current intra-oral dental sensors suffer from several drawbacks that manufacturers would like to circumvent.

They are often uncomfortable for the patient because of the sharp angles of the casing which tends to follow the rectangular shape of the silicon sensor that it contains. The constituent material of the casing is hard, for essential mechanical strength reasons, and somewhat unpleasant in terms of sensation in the mouth. The hardness of the material is required in practice so that the internal electronic circuits in the casing are protected from shocks (for example should it be dropped) by a sheet of foam or elastomer interposed between the electronic circuits and the wall of the casing, or even by sheets of other materials having additional functions (aluminum foil or lead foil).

The sensors are most often black, a color which is unpleasant to the user's or even the practitioner's eyes. In this field, white would instead be expected, the usual color of medical apparatus symbolic of cleanliness. However, if the sensors are made white, or even colored, the risk of producing an undesirable image because of the ambient light would be high. This is because the casing is necessarily thin for size reasons, and is therefore relatively transparent, and the lighting in a dental practitioner's surgery is often very strong. In the absence of X-ray illumination, a non-black image would then appear on the screen placed in front of the dental practitioner or even in front of the patient—such a meaningless image is unwanted and ought not to appear, so as not to trouble the patient or the practitioner.

Since the casings are all black and geometrically very similar, the various manufacturers cannot easily differentiate their products from those of competitive manufacturers. However, manufacturers, and moreover purchasers too, wish to differentiate their products and those of their competitors, which differentiation is difficult if all the sensors are black, of the same shape and the same size.

More generally, the market for these sensors is demanding improvements in terms of comfort and ergonomics.

The objective of the present invention is to take into account these many constraints and to produce an intra-oral dental radiology image sensor which, without impairing the image acquisition functionality, is more pleasant in one's mouth and more pleasant to the eye, while at the same time being distinctive, strong and optimally protected from shocks.

To achieve this objective, the invention proposes an intra-oral dental radiology image sensor comprising an electronic image acquisition module and a molded casing made of a hard plastic, characterized in that the casing locally includes overmoldings made of a soft plastic having the consistency of smooth rubber, at least over the sharpest corners of the hard plastic on the outside of the casing and in internal areas of the hard plastic at places where the electronic module may bear.

The shape of the hard plastic part and the shape of the overmolded soft plastic on the hard plastic are defined in such a way that the outside of the casing is free of asperities, notably at transitions between overmolded soft plastic areas and overmolding-free hard plastic areas.

The hard plastic may be a semicrystalline material such as a polyamide. The softer plastic may be a copolymer of the SEBS (styrene/ethylene-butylene/styrene) type.

These plastics may be easily overmolded together by injection molding. The softer plastic is preferably white or colored. It may be printed with a design or with characters.

In one particular embodiment, the casing includes a projecting dome through which an electrical cable passes, and this dome consists only of the soft plastic.

In another embodiment, one part of the shell is specifically intended to form an area sensitive to the touch for the practitioner's finger so as to help him to position the sensor in the patient's mouth. This specific sensitive area is coated with the soft plastic having the consistency of smooth rubber.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout and wherein.

DESCRIPTION OF PREFERRED EMBODIMENTS

Figure 1:
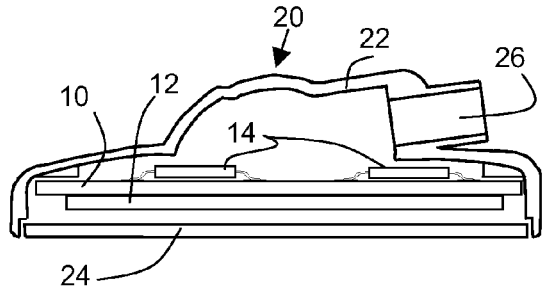
FIG. 1 shows a basic general view, in longitudinal section, of an intra-oral dental radiology image sensor in a hard plastic casing.
Figure 2:
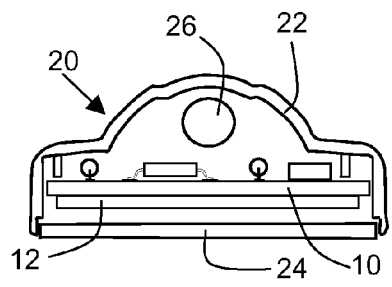
FIG. 2 shows a cross section of the casing of FIG. 1.

FIGS. 1 and 2 show the conventional basic construction of an intra-oral dental radiology sensor. Its lateral dimensions are a few centimeters in length and in width, the height being around one centimeter, so as to be able to be placed in a patient's mouth.

The sensor includes an electronic circuit card 10 on which an integrated circuit chip, constituting the actual matrix image sensor 12, and various discrete components 14 are mounted. In this example, the integrated circuit chip is mounted at the rear of the card 10 and the discrete components are mounted at the front.

The card is enclosed in a sealed casing 20 which comprises a shell 22 and a baseplate 24 which is welded to the shell after the card has been mounted in the cap. The shell is provided with a circular opening 26 through which a multiconductor electrical cable passes, said cable providing the connection between the card, on the inside of the casing, and the outside. The conductors of the cable are soldered to the electronic card or soldered to a connector which can be plugged into a complementary connector fixed to the card. The cable (not shown) is provided with an impermeable insulating jacket, the diameter of which matches the outline of the circular opening 26 so as to provide a seal between the outside and the inside of the casing.

In the prior art, the shell 22 and the baseplate 24 of the casing are made of a hard plastic and small sheets of impact-resistant foam (not shown) may be placed notably between the casing and the integrated circuit chip. To protect against shocks, the card could also be encapsulated with aluminum or lead foils, these also providing an electromagnet interference protection function. All these elements occupy a sizeable volume.

Figure 3:
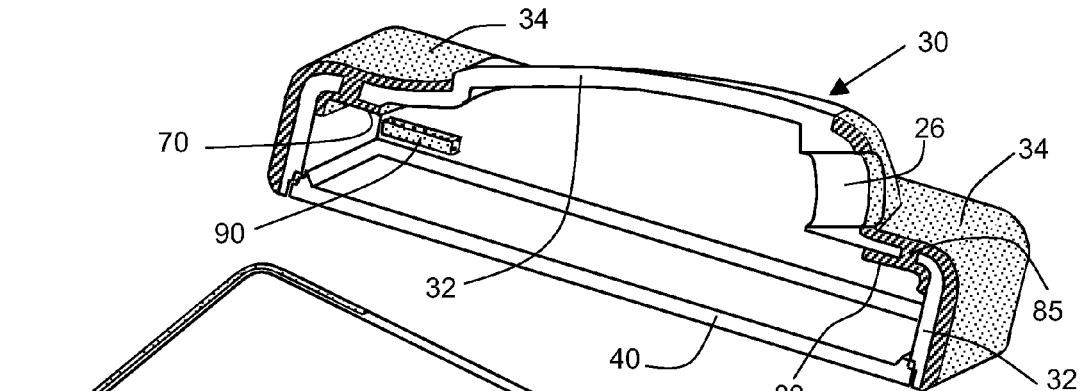
FIG. 3 shows a cut-away perspective view, from above, of an intra-oral dental radiology image sensor casing according to the invention.
Figure 4:
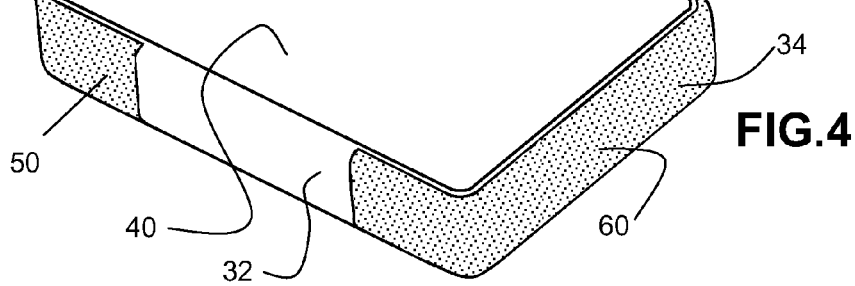
FIG. 4 shows a perspective view of the casing of FIG. 3 from below.
Figure 5:
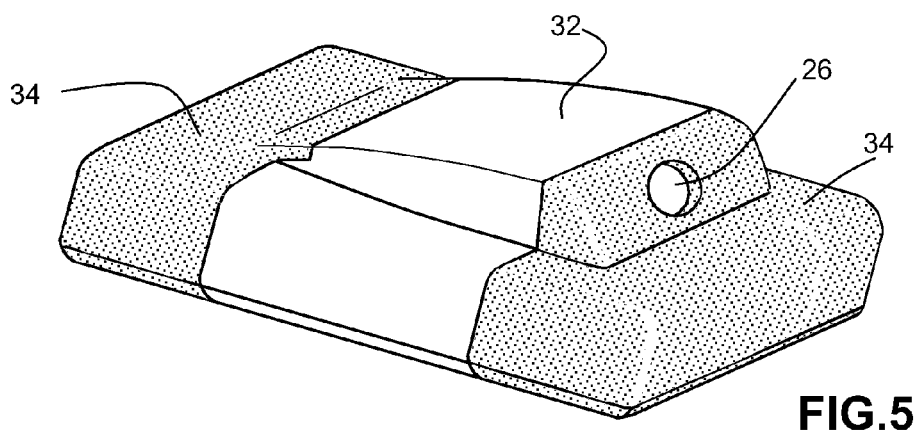
FIG. 5 shows a perspective view, not cut away, from above.

The principle of the casing according to the invention is shown in FIGS. 3 to 5. The casing is empty—the electronic card has not been shown inside.

The shell is denoted by 30 and the baseplate by 40. The shell consists of two different plastics welded together. The first plastic 32 is a hard plastic similar to that used previously. It is preferably black, so as to be as nontransparent to light as possible. This plastic may be a polyamide. The second plastic 34 is a soft plastic having the consistency of smooth rubber, such as an SEBS copolymer.

The surface of the second plastic is indicated by dots in the figures. The cross sections through this plastic are shown hatched. The surface and the cross sections of the first plastic are white.

The baseplate 40 that closes off the shell is preferably made only in the first rigid plastic. It is ultrasonically welded or bonded to the bottom rim of the shell, this rim being made in the first rigid plastic 32.

The plastic 34 having the consistency of smooth rubber is overmolded onto the first plastic and possesses rounded shapes so as to make the sharp corners of the first plastic 32 disappear. However, it is not overmolded over the entire external surface of the first plastic, as may be seen notably in FIGS. 4 and 4. Certain portions of the first plastic remain visible, i.e. not covered by the second plastic. In the example shown, there are two areas 50 and 60 made of the second plastic 34, one on the same side as the cable outlet (the opening 26) and the other on the opposite side. These areas completely surround the corners of the rectangular parallelepiped that the shell 30 basically forms and have a rounded shape around these corners.

The rigidity of the shell is mainly provided by the harder first plastic. The second plastic is bonded to the first during an overmolding operation. The configuration of the two parts 32 and 34 of the external surface of the shell is such that the transitions on the outside of the casing are smooth, that is to say the soft plastic overmolding does not produce asperities, i.e. neither recesses nor protrusions, where said overmolding joins hard plastic areas that are not covered. In addition, the entire external surface preferably has a smooth texture.

Moreover, the second plastic 34 is preferably also present inside the shell, in certain areas such as 70, 80, 90. The second plastic may serve as an impact-resistant cushion for the electronic card or the image sensor chip. Moreover, the rims, visible in FIGS. 1 and 2, for supporting the edges of the electronic card may now be produced by internal portions of the overmolded plastic 34. The area 90 visible in FIG. 3 may constitute such a support on which the card bears. Only a small element of the area 90 has been shown as an example, but it will be understood that the configuration of these areas may vary widely. A rim of soft plastic 34 may surround practically the entire internal periphery of the casing. The internal areas such as 80 are preferably connected to the external areas such as 50 and 60 via bridges 85 formed during the overmolding through openings in the first plastic, thereby keeping in place both the external plastic and the internal plastic. Openings are therefore provided when molding to form the shell made of the first plastic. During the overmolding of the first plastic with the second, the bridges 85 are formed through these openings.

The second plastic having the consistency of smooth rubber is preferably colored so as to make it attractive, but it may be white. The external light remains absorbed by the first plastic 32, which is preferably black.

What is thus obtained is a sensor that is simultaneously ergonomic (comfortable to be placed in one's mouth, because of the pleasant feel of the second plastic and because of the rounded corners that it has), mechanically strong because of the rigid plastic, and protected from shocks as regards the image sensor chip (protection provided by the internal areas of the second plastic). It is unnecessary to provide internal protection foam, so that the overall size may be reduced to a minimum. The electromagnetic shielding (by aluminum or lead) may be reduced or omitted in the case of CMOS image sensors which are less sensitive to electromagnetic interference.

Figure 6:
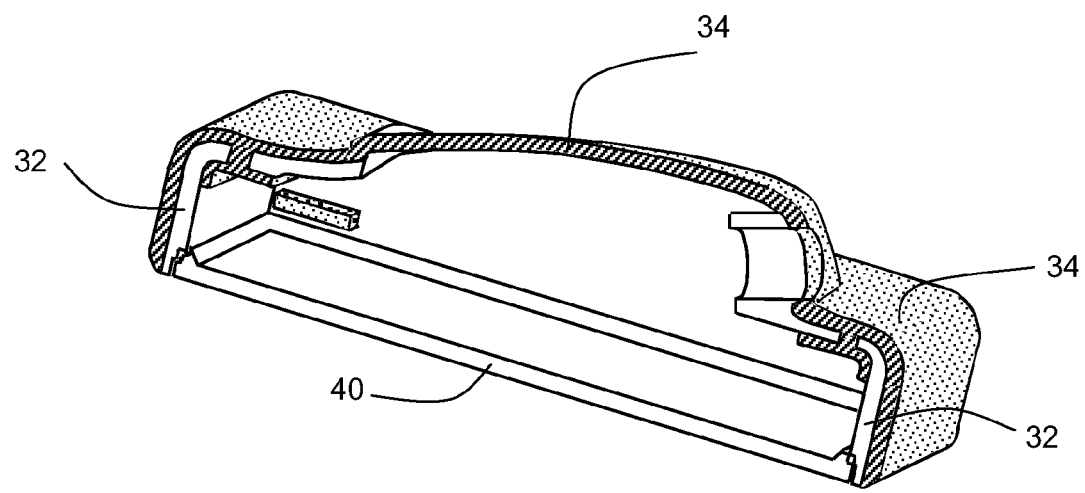
FIG. 6 shows, in cross section, an embodiment with a soft dome.
Figure 7:
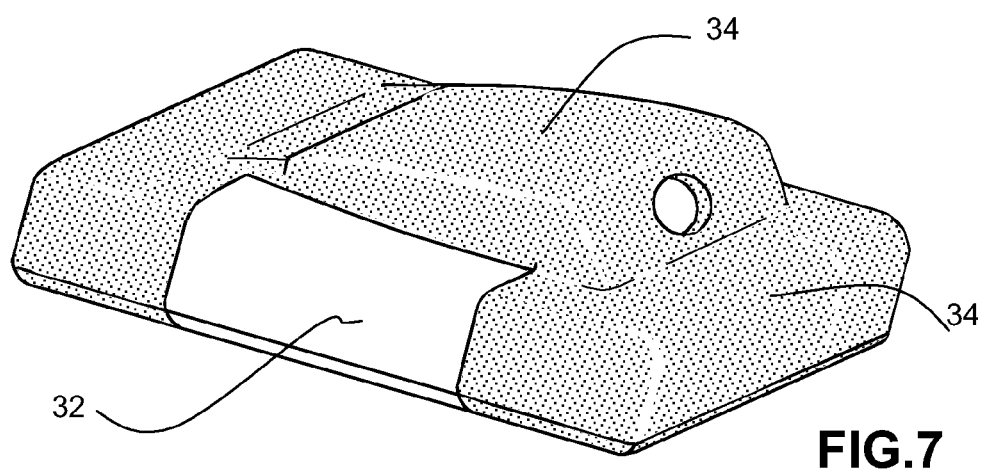
FIG. 7 shows, in perspective top view, the embodiment of FIG. 6.

Given that the overall shape of the intra-oral sensor is generally parallelepipedal but necessarily has a dome through which the connection cable to the outside passes, it is possible, in another embodiment, for this dome to be made in the second plastic, not overmolded at this point onto the first. In this embodiment, the dome is softer than the rest of the shell, which may prove to be particularly comfortable for the patient. FIGS. 6 and 7 show such a configuration in which the dome is formed only from the soft plastic which does not rest on the hard plastic. However, there is soft plastic continuity between the dome and other portions made of the soft plastic that rest on the hard plastic. In other words, the self-supported dome is integral with portions of soft plastic resting on the hard plastic, thereby ensuring that it is fastened to the rest of the casing.

The thickness of the layer of soft plastic 34 may be thinner on the dome than on the other parts of the shell.

In an alternative embodiment, an area of soft plastic may be provided which is specifically designed to help the practitioner to position the sensor inside the patient's mouth. This area is for example located toward the center of the shell (and it may be on the cable exit dome). Said area has for example a circular shape with a diameter of around one centimeter, i.e. a size corresponding to the area of a tip of a finger. The practitioner will feel this area and will be better able to feel what the position of the sensor in the mouth is.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by definition contained in the appended claims and equivalents thereof.

The invention claimed is:

1. An intra-oral dental radiology image sensor comprising an electronic image acquisition module and a molded casing made of a hard plastic, wherein the casing locally includes overmoldings made of a softer plastic having the consistency of smooth rubber covering the hard plastic in areas located on the outside of the casing and corresponding to projecting angular portions of the hard plastic, and also in areas located inside the casing at places where the electronic module may bear.

2. The radiology image sensor as claimed in claim 1, wherein the hard plastic is a polyamide.

3. The radiology image sensor as claimed in claim 2, wherein the soft plastic overmolded parts inside the casing are connected to soft plastic parts on the outside of the casing via bridges formed in openings provided in the hard plastic parts.

4. The radiology image sensor as claimed in claim 2, wherein the soft plastic is an SEBS (styrene/ethylene-butylene/styrene) copolymer.

5. The radiology image sensor as claimed in claim 1, wherein the soft plastic is an SEBS (styrene/ethylene-butylene/styrene) copolymer.

6. The radiology image sensor as claimed in claim 5, wherein the soft plastic overmolded parts inside the casing are connected to soft plastic parts on the outside of the casing via bridges formed in openings provided in the hard plastic parts.

7. The radiology image sensor as claimed in claim 1, wherein the soft plastic overmolded parts inside the casing are connected to soft plastic parts on the outside of the casing via bridges formed in openings provided in the hard plastic parts.

8. The radiology image sensor as claimed in claim 7, wherein the soft plastic is an SEBS (styrene/ethylene-butylene/styrene) copolymer.

9. The radiology image sensor as claimed in claim 1, wherein one part of the shell is specifically intended to form an area sensitive to the touch for the practitioner's finger so as to help him to position the sensor in the patient's mouth, this specific sensitive area being coated with the soft plastic having the consistency of smooth rubber.

10. The radiology image sensor as claimed in claim 9, wherein the soft plastic overmolded parts inside the casing are connected to soft plastic parts on the outside of the casing via bridges formed in openings provided in the hard plastic parts.

11. The radiology image sensor as claimed in claim 9, wherein the soft plastic is an SEBS (styrene/ethylene-butylene/styrene) copolymer.

12. The radiology image sensor as claimed in claim 1, wherein the casing includes a dome through which a cable passes, and this dome consists only of soft plastic, not resting on hard plastic but fastened to other soft plastic portions resting on hard plastic.

13. The radiology image sensor as claimed in claim 12, wherein the soft plastic overmolded parts inside the casing are connected to soft plastic parts on the outside of the casing via bridges formed in openings provided in the hard plastic parts.

14. The radiology image sensor as claimed in claim 12, wherein the soft plastic is an SEBS (styrene/ethylene-butylene/styrene) copolymer.

15. The dental radiology image sensor as claimed in claim 1, wherein the casing is formed from a shell and a baseplate welded to the shell, the shell having soft plastic overmolded areas.

16. The dental radiology image sensor as claimed in claim 15, wherein the baseplate is ultrasonically welded to a hard plastic part of the shell.

17. The radiology image sensor as claimed in claim 16, wherein the soft plastic overmolded parts inside the casing are connected to soft plastic parts on the outside of the casing via bridges formed in openings provided in the hard plastic parts.

18. The radiology image sensor as claimed in claim 16, wherein the soft plastic is an SEBS (styrene/ethylene-butylene/styrene) copolymer.

19. The radiology image sensor as claimed in claim 15, wherein the soft plastic overmolded parts inside the casing are connected to soft plastic parts on the outside of the casing via bridges formed in openings provided in the hard plastic parts.

20. The radiology image sensor as claimed in claim 15, wherein the soft plastic is an SEBS (styrene/ethylene-butylene/styrene) copolymer.

* * * * *